US012599777B1

(12) United States Patent

Kovanen

(10) Patent No.: US 12,599,777 B1

(45) Date of Patent: Apr. 14, 2026

(54) MAGNETIC PULSE THERAPY DEVICE (MPTD) HIGH-POWER APPLICATOR FOR FOOT

(71) Applicant: Innovator Corporation, Browns Point, WA (US)

(72) Inventor: David Kovanen, Browns Point, WA (US)

(73) Assignee: Innovator Corporation, Browns Point, WA (US)

( * ) Notice: Subject to any disclaimer, the term of this patent is extended or adjusted under 35 U.S.C. 154(b) by 0 days.

(21) Appl. No.: 19/096,292

(22) Filed: Mar. 31, 2025

Related U.S. Application Data

(63) Continuation-in-part of application No. 19/072,219, filed on Mar. 6, 2025, now Pat. No. 12,415,087, which is a continuation-in-part of application No. 18/905,994, filed on Oct. 3, 2024, now Pat. No. 12,377,281, which is a continuation of application No. 18/432,044, filed on Feb. 4, 2024, now Pat. No. 12,268,891.

(51) Int. Cl.
  A61N 2/02 (2006.01)
  A61N 2/00 (2006.01)

(52) U.S. Cl.
  CPC ............... A61N 2/02 (2013.01); A61N 2/008 (2013.01)

(58) Field of Classification Search
  CPC .................................. A61N 2/02; A61N 2/008
  See application file for complete search history.

(56) References Cited

U.S. PATENT DOCUMENTS

| | | | |
|---|---|---|---|
| 4,757,804 A | | 7/1988 | Griffeth |
| 5,314,401 A | * | 5/1994 | Tepper .................... A61N 2/02 |
| | | | 600/15 |
| 6,132,362 A | | 10/2000 | Tepper |
| 9,550,067 B1 | | 1/2017 | Fischell |
| 9,849,302 B1 | | 12/2017 | Fischell |
| 10,369,373 B2 | | 8/2019 | Leung |
| 10,589,117 B1 | | 3/2020 | Fischell |
| 2002/0151760 A1 | | 10/2002 | Paturu |

(Continued)

FOREIGN PATENT DOCUMENTS

| | | |
|---|---|---|
| CN | 112494815 A | 3/2021 |
| CN | 216319524 U | 4/2022 |
| WO | 2023/100130 | 6/2023 |

OTHER PUBLICATIONS

International Commission on Non-Ionizing Radiation Protection (ICNIRP), Guidelines for limiting exposure to time-varying electric and magnetic fields (1 Hz to 100 KHz), Jun. 15, 2010, Health Physics.

*Primary Examiner* — Carrie R Dorna
*Assistant Examiner* — Joshua Daryl D Lannu
(74) *Attorney, Agent, or Firm* — Stevens Patent Law LLC; James Stevens; Dat Mai

(57) ABSTRACT

A magnetic pulse therapy applicator configured to deliver high intensity pulsed electromagnetic field (PEMF) therapy to a user's foot. The applicator allows the user to slide their foot into and out of the treatment area with minimal effort and automatically positions the foot within the core of a High-Power solenoid that generates therapeutic magnetic pulses. The solenoid is enclosed within a housing designed for efficient heat dissipation through air cooling, oil cooling, or both, enabling sustained high-power operation.

28 Claims, 17 Drawing Sheets

(56)              References Cited

U.S. PATENT DOCUMENTS

| | | | |
|---|---|---|---|
| 2003/0132668 A1* | 7/2003 | Lanni | H02J 7/00047 |
| | | | 307/38 |
| 2003/0158585 A1 | 8/2003 | Burnett | |
| 2005/0261542 A1* | 11/2005 | Riehl | A61N 2/006 |
| | | | 600/14 |
| 2006/0241333 A1* | 10/2006 | Hunter | A61N 2/008 |
| | | | 600/13 |
| 2014/0249354 A1 | 9/2014 | Anderson | |
| 2015/0360045 A1* | 12/2015 | Fischell | A61N 2/02 |
| | | | 600/14 |
| 2017/0188882 A1* | 7/2017 | Foster | H01F 27/2804 |
| 2018/0104504 A1* | 4/2018 | Jin | A61N 2/02 |
| 2019/0310333 A1* | 10/2019 | Ham | G01R 33/3804 |
| 2023/0215554 A1* | 7/2023 | Roh | A61B 5/6846 |

* cited by examiner

110

100

120

100

210

100

300

100

300

500

1200

1620

1625

1520

1615

1610

1700

1710

1700

1720

MAGNETIC PULSE THERAPY DEVICE (MPTD) HIGH-POWER APPLICATOR FOR FOOT

BACKGROUND OF THE INVENTION

More than a million Americans suffer from severe neuropathic pain in their feet. More than a third of people with diabetes suffer chronic pain from Diabetic Peripheral Neuropathy (DPN). An estimated 20 million Americans suffer from plantar fasciitis.

TECHNICAL FIELD OF THE INVENTION

This disclosure relates to the field of medical devices, specifically magnetic pulse therapy devices (MPTDs).

BACKGROUND ART

It is estimated that more than 20 million Americans experience "impactful" levels of neuropathic pain levels that severely degrade their ability to function. Worldwide the numbers are estimated to exceed 300 million people.

There are presently no good treatments for this type of pain as it is especially resistant to pharmaceuticals. The pain is so severe that it is considered to be one of the worst pains a person can experience, and it does drive people to suicide.

Strong repetitive magnetic pulses can induce an analgesic or antinociceptive effect with significant and sustained duration, even when pharmaceuticals have been ineffective. Studies have shown this pain relief to be effective in the majority of cases, with reductions in pain intensity ranging from 50% to 100%. The effects often last for weeks or months, and in some cases, some of the pain reduction may be permanent. There are no known adverse side effects from repetitive magnetic pulse stipulation.

Encouragingly, some people with Diabetic Peripheral Neuropathy, a condition often characterized by both pain and numbness, report a partial regaining of feeling in areas previously devoid of sensation following MPTD therapy.

PRIOR ART

High Power MPTDs are for Clinical Use

For the purposes of the present application, the term "high power" means any MPTD which operates outside of (in excess of) the guidelines for exposure limits for the general public (considering all health conditions) established by the International Commission on Non-Ionizing Radiation Protection (ICNIRP) in their 2010 publication. "Guidelines for limiting exposure to Time-varying electric and magnetic fields (1 Hz to 100 khz)" published in Health Physics, 99 (6), 818-836. The ICNIRP (2010).

Almost all clinical Magnetic Pulse Therapy Devices (MPTDs) in use today are high power MPTDs that generally employ pulses with a flux density (B) between 300 mT and 3,000 mT. A strength of 1,500 mT (1.5 T) is typical for an MPTD device used in a clinic and a strength of 700 mT is common for treating Peripheral Neuropathy in a clinic.

High power is preferred for both their speed and ease of effective treatment. A clinic needs to quickly treat and discharge a patient, often within 10 to 20 minutes. A High-Power device delivers dosages quickly. Patients also achieve more immediate results. The use of high power means more dosage ($\Sigma\Delta B$) is delivered within a treatment session, and the goal is to quickly administer a certain dosage. high power therefore allows patients to be treated quickly, accommodates irregular coverage, compensates for lower quality magnetic flux, and better fills in the gaps. high power accommodates irregular coverage, compensates for lower quality (non-coherent) magnetic flux, and better fills in the gaps. high power MPTD systems are practical for a clinical environment where they are used throughout the day with their high cost amortized across many patients.

A High-Power MPTD applicator is typically attached via a thick cable to an energizing control unit that contains the source of high voltage and high amperage pulses. These power levels may approach a megawatt on an instantaneous basis. Both voltages and amperages can exceed 1000 (V≥1,000 and A≥1,000). Amperages can approach 10,000 amperes in some implementations.

This high power generates substantial heat within the applicator. It is typical for an applicator to reach its maximum safe operating temperature after about 10 to 15 minutes of use. For this reason, manually operated high power applicator coils may require liquid cooling or they may need to be swapped with a pre-cooled manual applicator which was stored within a nearby ice chest. Swapping manual applicators require unplugging the thick power cables, thereby exposing a connector potentially with lethal voltages and amperages; extra safety precautions are therefore required.

High Power Applicators for the Foot

Neuropathic pain almost always begins in the toes and then progresses into the foot. In more advanced stages it can progress into what is called a "socks and gloves" configuration where it also affects the fingers and hands.

The greatest need is an applicator that can administer strong magnetic pulses to the feet, especially the forefoot and particularly the toes.

Any attempt at making these foot-specific applicators is severely dysfunctional. The most common problem is the risk of what is called "thermal runaway" where an applicator accumulates heat faster than it can be dissipated, thereby getting hotter and hotter until it reaches sealding temperatures. As a sense of temperature is commonly lost by people with peripheral neuropathy, the risk of cooking the patient's foot is a possibility.

Shoe Style Applicator

U.S. Pat. No. 9,550,067 ('067) is a purpose-built High-Power foot-specific applicator. The '067 applicator essentially wraps a single massive coil around a foot. The result is an applicator that is heavy and inflexible and probably dangerous.

The production of large amounts of heat in combination with being padded with a thick foam rubber lining (column 2 line 61) results in a well-insulated shoe that presents a fire hazard. The thermal issues inherent in the '067 design are acknowledged in the disclosure.

Ingress and egress of the foot into the applicator disclosed in the '067 patent is very problematic: It has no apparent opening; it is padded with insulating foam; the weight from the rather massive #2 to #6 AWG coils make it heavy; the connecting cable makes it immobile; a foot that is painful to the touch because of neuropathy is not easily manipulated.

Sandal Style Applicator

U.S. Pat. No. 9,849,302 ('302) is a purpose-built high power MPTD that has an applicator designed for applying magnetic pulses to a foot. In this invention, it is disclosed that precisely three coils are be positioned into a co-planar formation resembling a sandal.

The '302 is a high power MPTD, the specification states that "it would be typical to have a peak electrical current in the coil that could be as small as 500 Amperes or as strong as 10,000 Amperes. The peak pulse voltage to accomplish these intense levels of electrical current could be between 500 and 10,000 volts." (column 3 line 59) The coils in the '302 device are constructed from #6 to #12 AWG (Column 7 at line 60) wire or conflictingly of #2 to #8 AWG wire (Column 5 at line 32). This is typical sizing for a high power MPTD.

The '302 patent states that the coils typically have 10 to 30 turns of wire up to #2 AWG. Since #2 AWG wire is approximately a quarter of an inch in diameter (plus insulation for up to 10,000 volts) this suggests that the coils may be 2 to 6 inches tall, and quite heavy. The '302 patent proposes using Velcro straps to hold the three coils in place, but this seems improbable given the bulk and weight and also tug of thick connecting cables. Even if accomplished, this "sandal" could look nothing like what is depicted in FIG. 6. It is not convenient at all, it would be difficult to "gear up" a patient with such bulky, heavy coils.

The '302 patent discusses the need to use rubber or other lining to minimize the number of different sizes required. Thermal injury of the foot from the sandal remains a possibility.

Recognizing the inherent thermal problems with its design, the '302 patent suggests forming the coil conductors into tubes so that gas or water can flow through them to provide cooling. Forming the coil conductors into tubes creates more problems. Tube-shaped conductors would necessarily result in lower density windings resulting in less overall flux produced, requiring more amperage to compensate, which would generate even more heat. Ignoring the sheer complexity of constructing the coils from water-filled electrically insulated tubing carrying up to 10,000 volts, it would be problematic to do this within the form factor of a sneaker. The '302 patent offers no suggestion of how this is possible.

The '302 patent further discloses that the (precisely) three coils can be sequentially operated. The disclosed benefit is that because the inductance of each of the three coils is lower than a single coil so the amperage could be higher. But alas, such an arrangement would triple the amperage, triple wiring in the cable connecting the applicator with the pulse generator and manipulating the three large and thick formed coils remains problematic. Presumably monitoring and managing the thermal risks from three separate coils is similarly magnified.

There is another, even more troubling aspect to the '302 disclosure and that is the flux cancelation effect of having three nearby co-planar coils. The actual reason for separately powering the coils in the sandal design is that they must be separately energized as they would partly cancel each other out if concurrently energized. There is no combination of coil polarities for these three co-planar coils which doesn't result in flux cancelation. The proposed (precisely) three coil arrangement is oblivious to this cancelation effect, or else that is the real reason that the coils must be energized separately, sequentially.

The '302 patent asserts that having straight wires that are generally flat on the bottom of the sandal minimizes heating. The science behind this novel assertion is dubious.

The sandal applicator of '302 therefore has thermal problems, ingress/egress problems, dosing of magnetic flux has non-uniform coverage, and it is simply not feasible to construct the sandal as illustrated. The toes overhang the applicator, the tibial nerve in the inner ankle is not close to any coil, and only one side of the heel is treated. This invention may be more of an idea than something that can actually be constructed.

Patent '302 illustrates once again that an applicator in a shoe or sandal formation is a difficult problem to solve.
Integrated Style Applicator U.S. Pat. No. 10,589,117 ('117) creates several new problems.

The device disclosed in '117 integrates the applicator into the same housing as the energizing electronics, thereby eliminating the connecting cable harness. It also has an applicator that is a rigid shelf that the foot can be placed upon or under; this is in contrast with the enclosed sneaker of the '067 and '302 devices.

The use of a shelf potentially overcomes the thermal runaway and foot-insertion problems inherent in the '067 and '302 designs. In these respects, '117 device improves upon '067 and '302 devices.

The '117 device has an applicator that consists of a single co-planar coil formed into the shape of a shelf. The patient's foot may be placed on top of the shelf so that the plantar surface and toes can be treated or alternatively the patient's foot may be placed beneath the shelf so as to treat the toes and dorsum surface of the foot. The '117 disclosure suggests that a patient can treat other parts of the foot but doesn't provide adequate disclosure on what contortions are necessary to accomplish this. However, this is to be accomplished, treating the plantar and dorsum surfaces of the foot is necessarily a multi-step process requiring repositioning the foot and extra treatment time.

The device disclosed in '117 is not without serious limitations. The coils produce significant amounts of heat. While not specifically addressed in the '117 specification, the particular layout disclosed would likely also suffer from "eddy current heating" where the device has a tendency to heat itself, beyond the heat that the coils produce. A high power MPTD by its very nature produces pulses of high magnetic flux and when the flux field lines meet a horizontal conductive material, they will produce eddy currents which can create substantial amounts of heat. There is no indication of any awareness of this in the '117 configuration. The '117 disclosure presents no way of dissipating this substantial heat.

The '117 device appears to anticipate and address this problem by suggesting power levels that may be reduced by 80% to just 300 mT, or about 20% of what is typical for a high power clinical MPTD. It is likely that the reduced power is an effort to keep temperatures under control.

The '117 patent offers numerous advancements and once again points out the need for a MPTD to treat the foot for nerve pain. This invention illustrates once again that a truly good applicator for the foot remains an unsolved and long felt problem.

SUMMARY OF THE INVENTION

Until now, two issues have prevented a high-power foot-specific applicator from being viable: 1) heat dissipation and thermal issues, and 2) difficulty of donning and doffing a device comprised of coils constructed from massive windings.

The present application solves both of these issues by adapting the original application's mid-power design for use in a high power MPTD. The adaptations are straightforward to implement because of the unique design of the applicator in the original application. The present application adapts the unique applicator shape in the original application for use with thick wire windings which are required for a high power MPTD.

The easy donning and doffing features of the applicator in the original application are unchanged. Donning and doffing remain as easy as sliding one's foot in and out. It is a simple and natural horizontal movement and there are no obstacles to navigate, and no closures are functionally necessary.

The task of dissipating heat from high power coils becomes possible because of the original application's rigid housing that encloses the high-power coils and treatment cavity. Normally, enclosing high power coils would be the opposite of what you want to do as it traps heat. But the present application uses this weakness to advantage. The interstitial area between the outer enclosure and the treatment chamber is where the high-power coils are positioned. This is an enclosed space of significant volume. It can be filled with oil or forced air can be directed through it.

If using oil, the heat produced within the coils is transferred to the oil and then subsequently transferred to the heat sink. If using forced air, a blower or fan draws air into the interstitial area, across the coils, and then exhausts it. Both approaches are effective and that take advantage of the same overall shape and design as in the original application.

With these relatively minor changes the applicator from the original application can be adapted for high power use while retaining the benefits of safety, thermal management, and simplicity.

The applicator in the present application also maintains the benefit that the foot is inserted into the core of a solenoid and thereby gets the benefit of powerful coherent core flux.

6

Figure 9A:
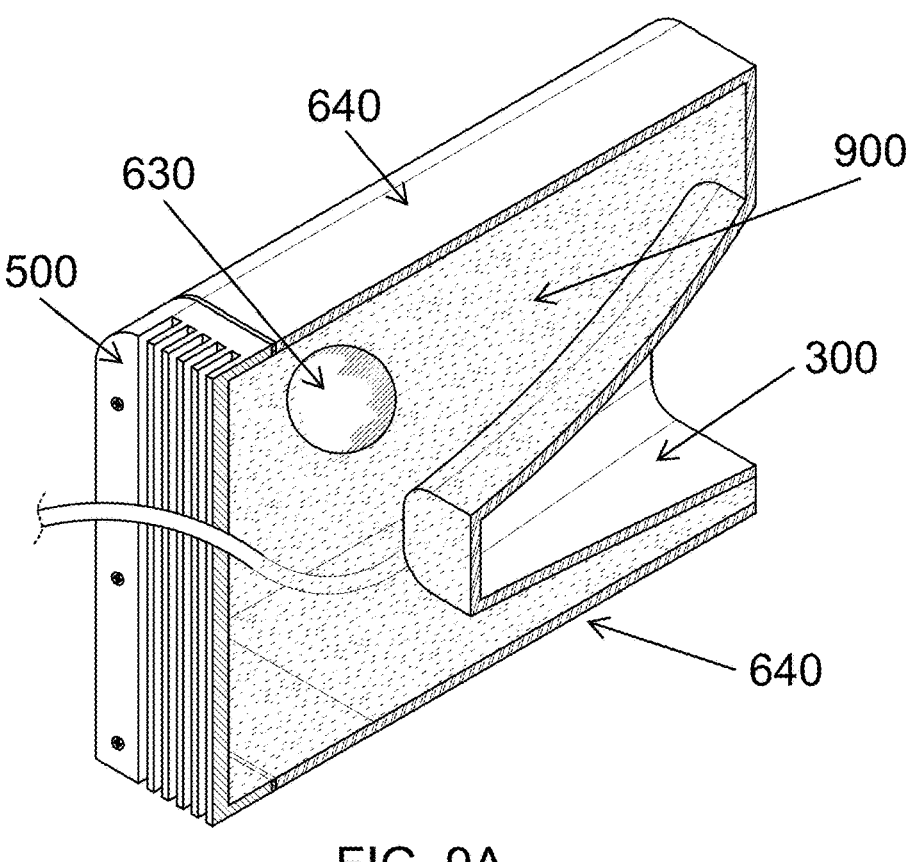
FIG. 9A shows a cross-sectional view of the MPTD applicator highlighting the outer housing (640) and its interstitial area (900) filled with dielectric oil, thermal expansion ball (630), treatment chamber (300), heat sink (500), and housing (640).
Figure 9B:

FIG. 9B depicts a cross-sectional view of the MPTD applicator housing (640) containing solenoid coils (620) positioned in the interstitial area (900), thermal expansion ball (630), treatment chamber (300), heat sink (500), and housing (640).

Figure 10A:
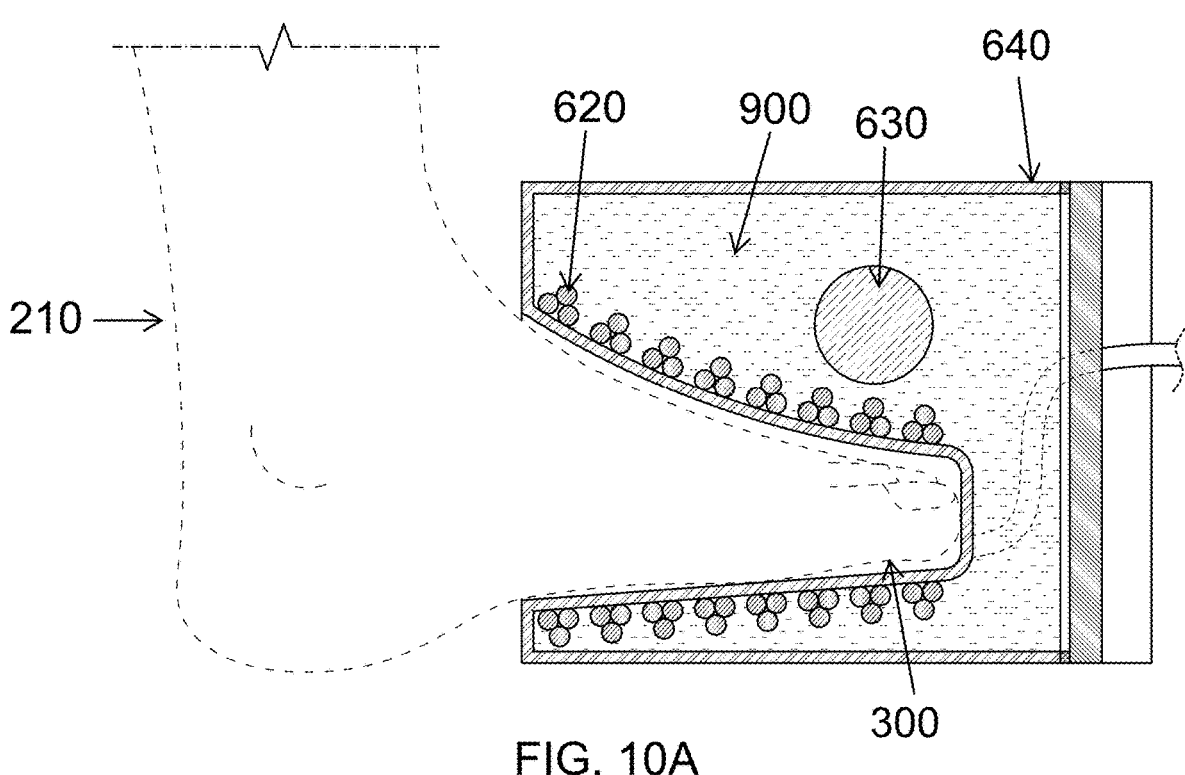

FIG. 10A illustrates a cross-sectional side view of the applicator and housing (640) showing a foot (210) inserted into the treatment chamber (300) with the interstitial area (900) filled with oil, solenoid coils (620), and thermal expansion ball (630).

Figure 10B:
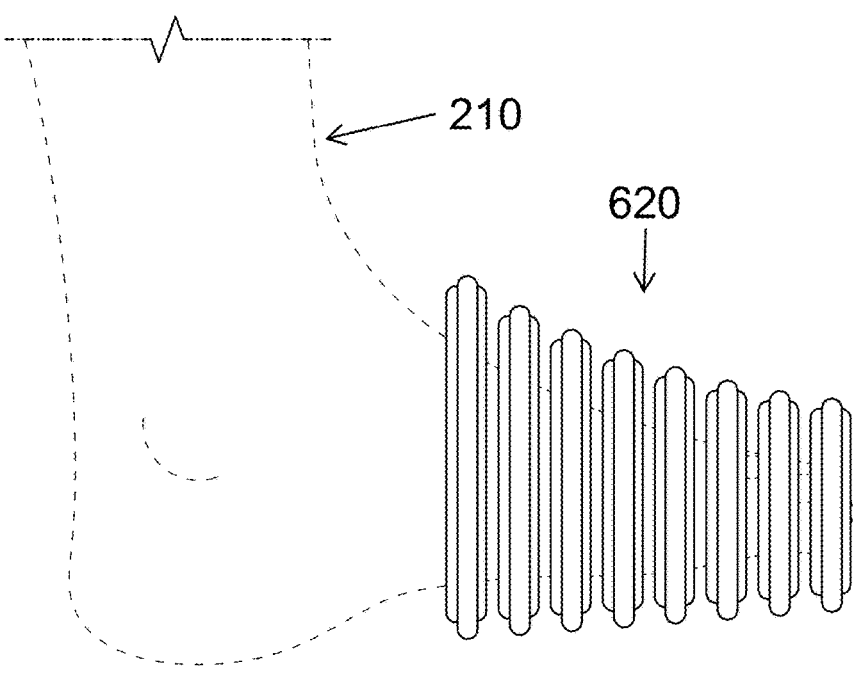

FIG. 10B illustrates a cross-sectional side view showing a foot (210) inserted into the surrounding solenoid coils (620). This illustrates that the treatment coils (620) in FIG. 10A encircle the foot (210).

Figures 11A, 11B:
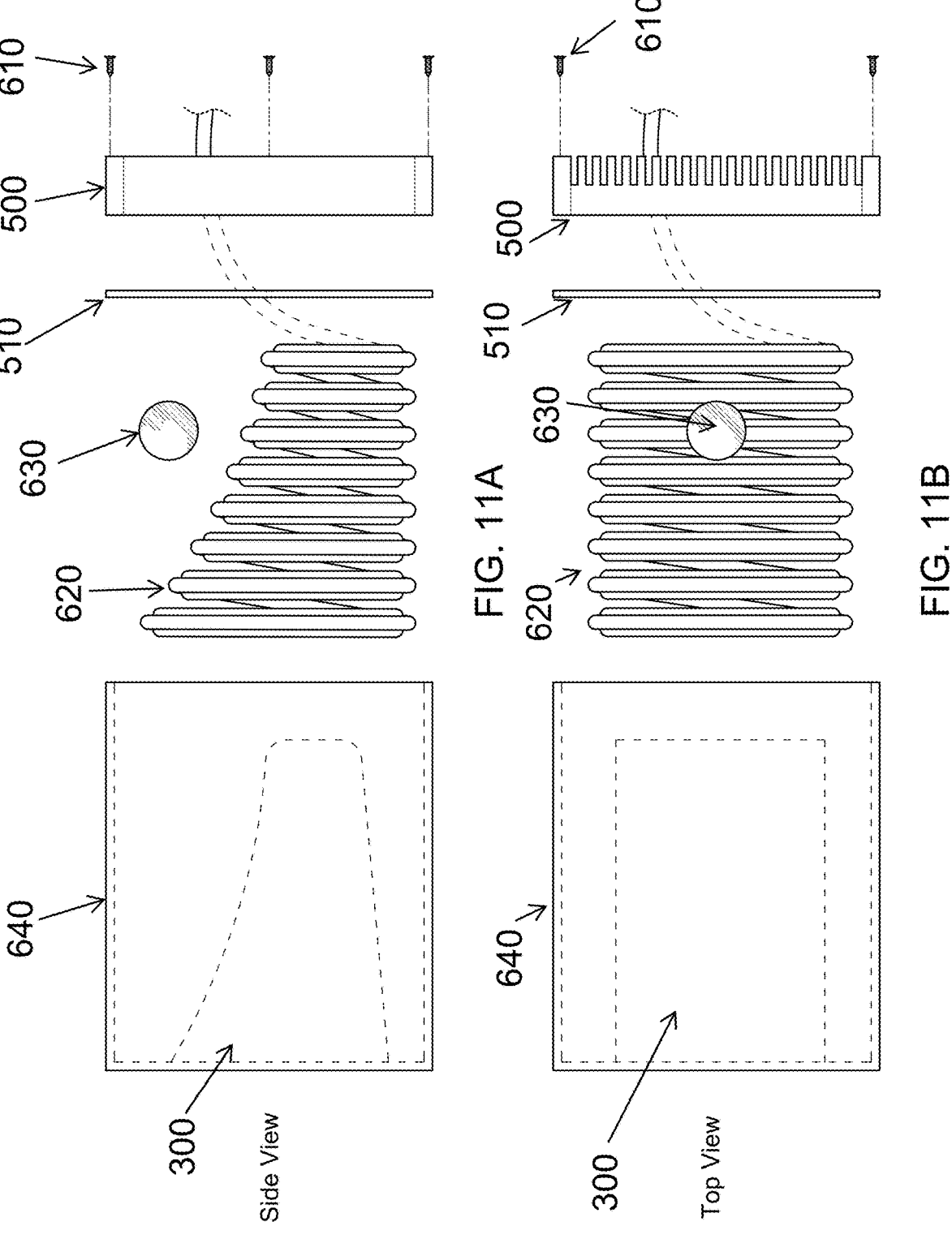

FIG. 11A depicts a side view assembly drawing of the MPTD applicator with housing (640) which contains the integrated treatment chamber (300), the coils (620) which can slide over the integrated treatment chamber (300), the thermal expansion ball (630), the gasket (510), heat sink (500), and screws (610).

FIG. 11B shows a top view assembly drawing of the MPTD applicator with housing (640) which contains the integrated treatment chamber (300), the coils (620) which can slide over the integrated treatment chamber (300), the thermal expansion ball (630), the gasket (510), heat sink (500), and screws (610).

Figure 12:
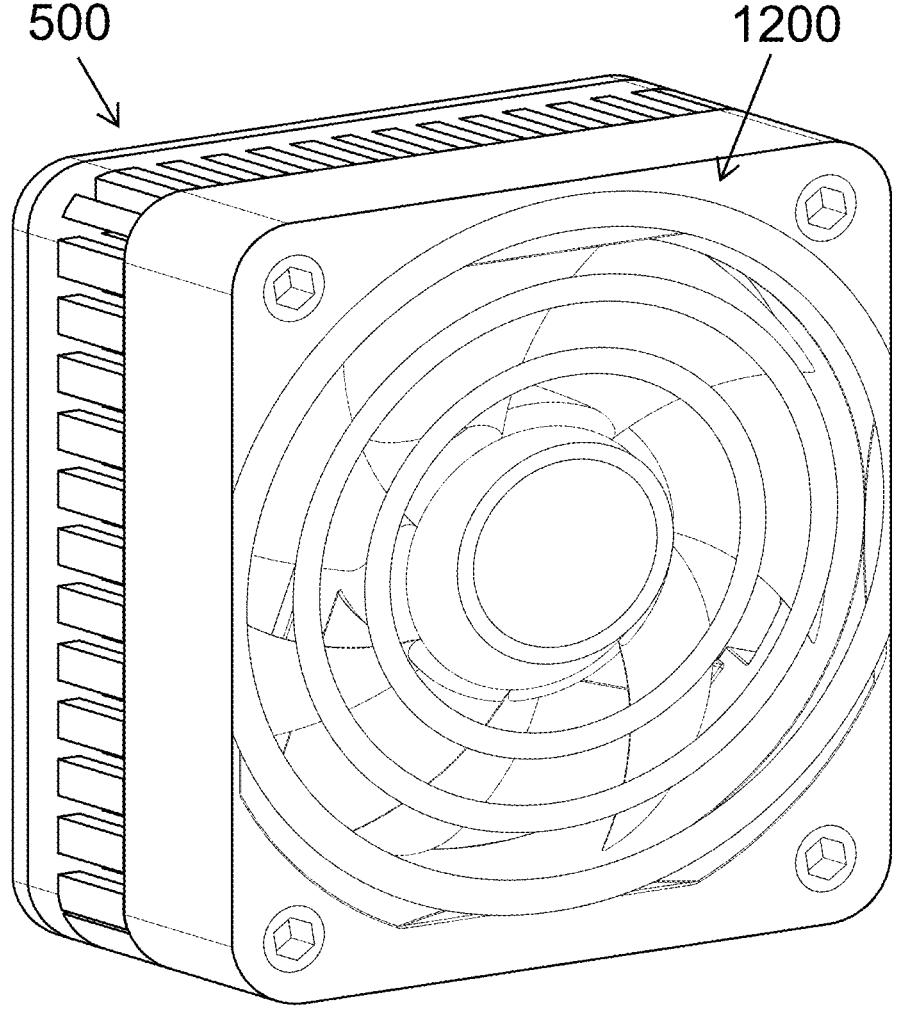

FIG. 12 illustrates a heat sink (500) and an attached fan assembly (1200).

Figure 13A:
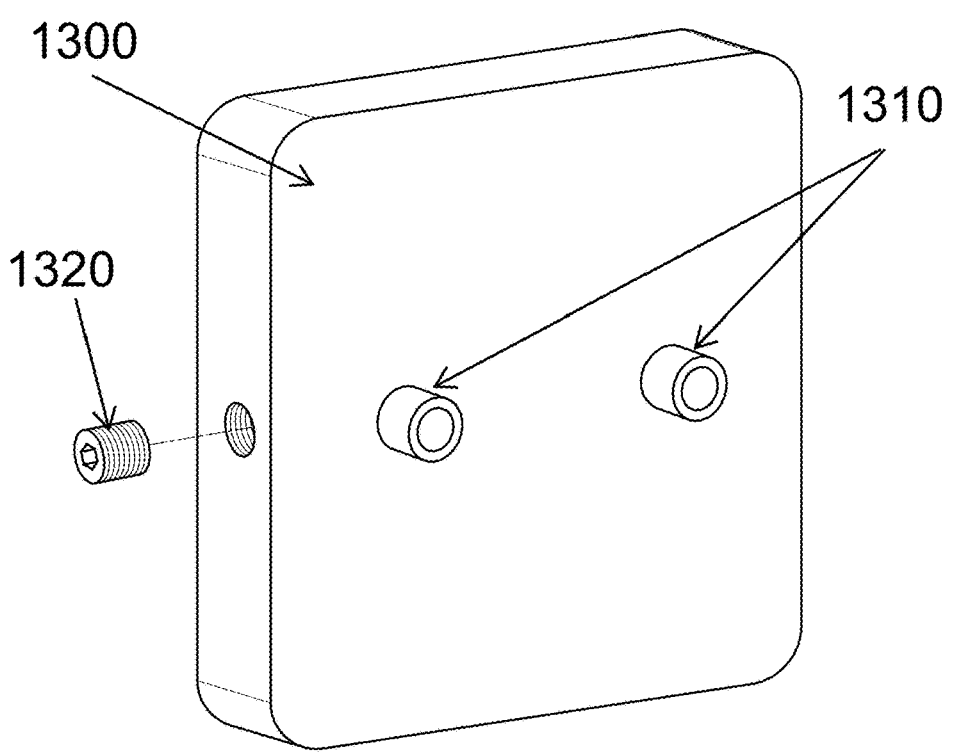

FIG. 13A shows a heat exchanger endcap (1300) for a closed loop liquid external cooling system, liquid inlet/outlets (1310) and a plug (1320).

Figure 13B:
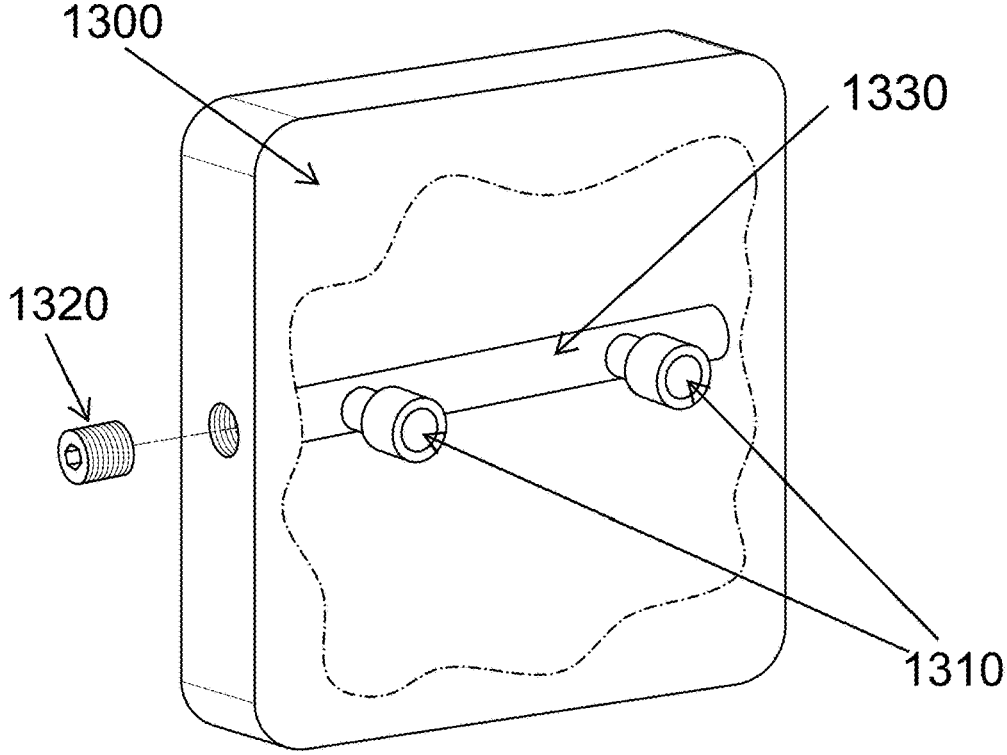

FIG. 13B depicts a cut-away view of a closed loop heat exchanger end cap (1300) showing the internal heat exchanger (1330) showing the connection to the inlets/outlets (1310) and the plug (1320).

Figure 14:
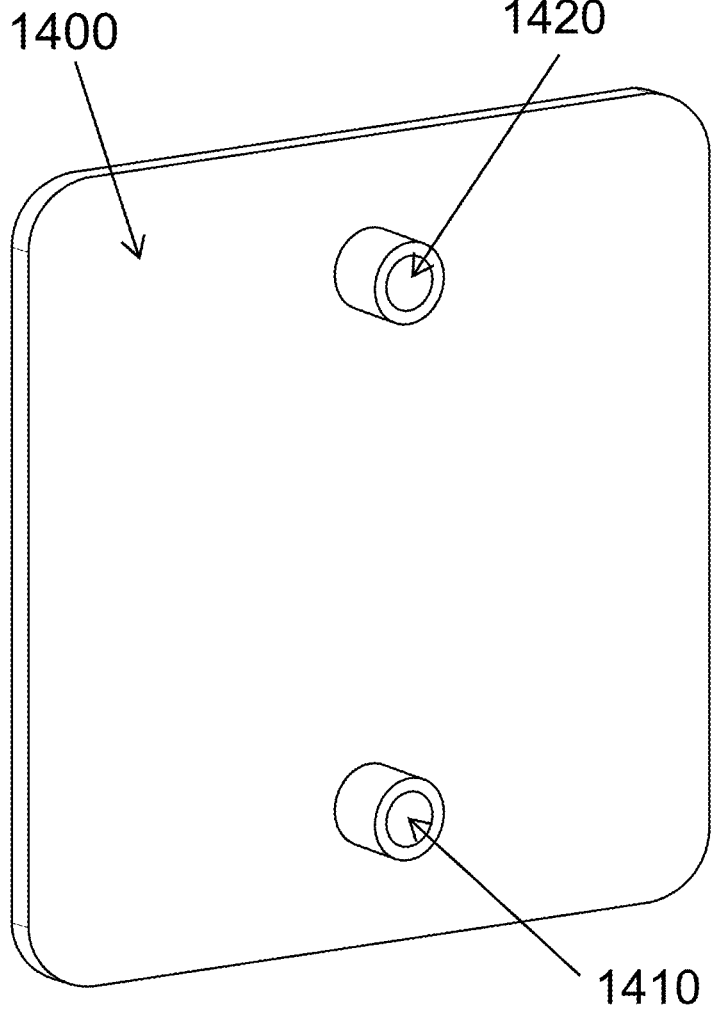

FIG. 14 shows an open loop heat exchanger (1400) with a connector inlet (1410) for cooled oil and a connector outlet (1420) for oil to return to an external cooling system.

Figure 15:
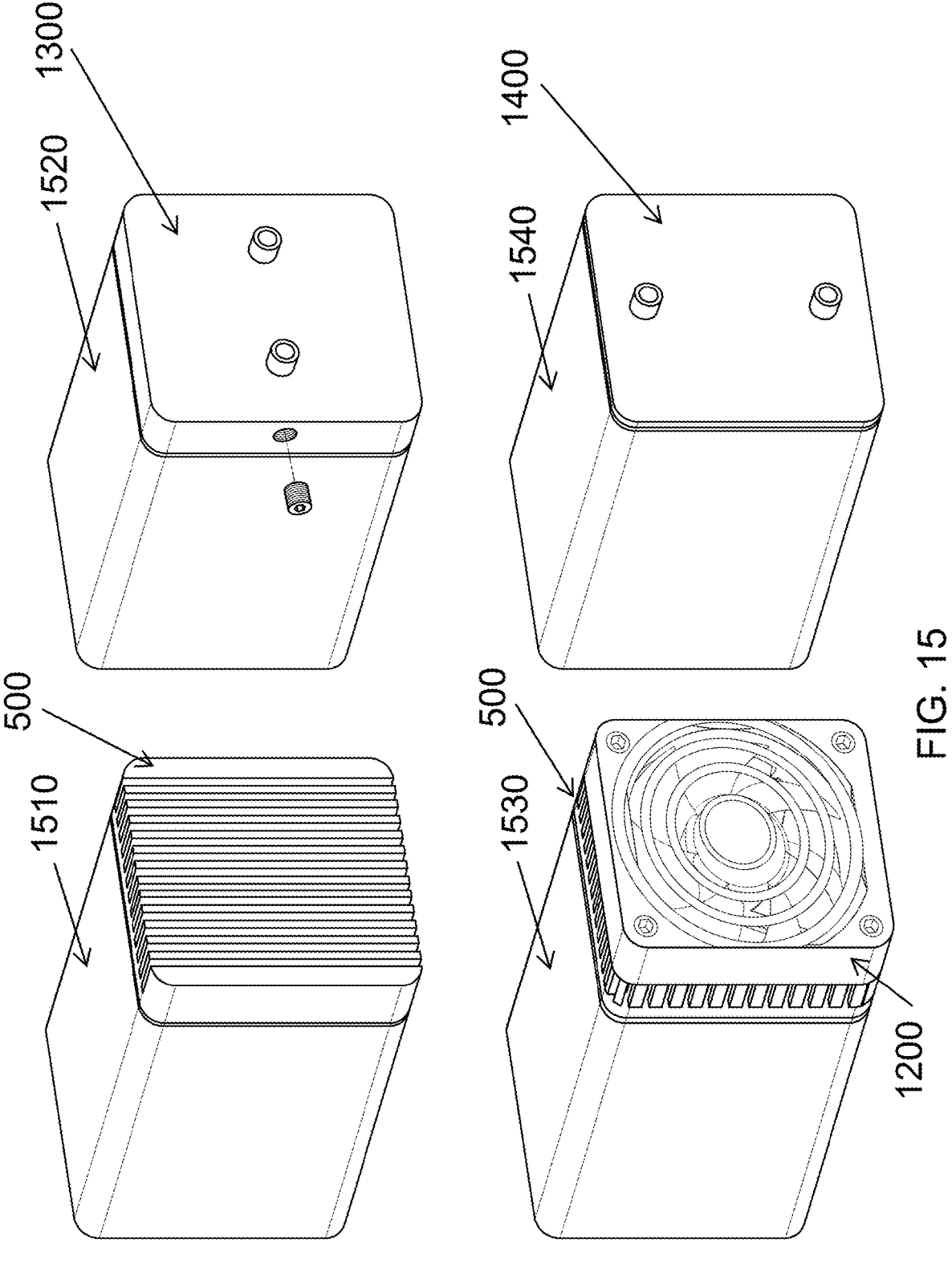

FIG. 15 shows various configurations of the heat dissipation system including passive (1510) with heat sink (500), closed loop (1520) with closed loop heat exchanger (1300), open loop (1540) with oil tube connection end-plate (1400), ambient air cooling (1530) with heat sink (500) shown with forced air cooling fan (1200).

Figure 16:
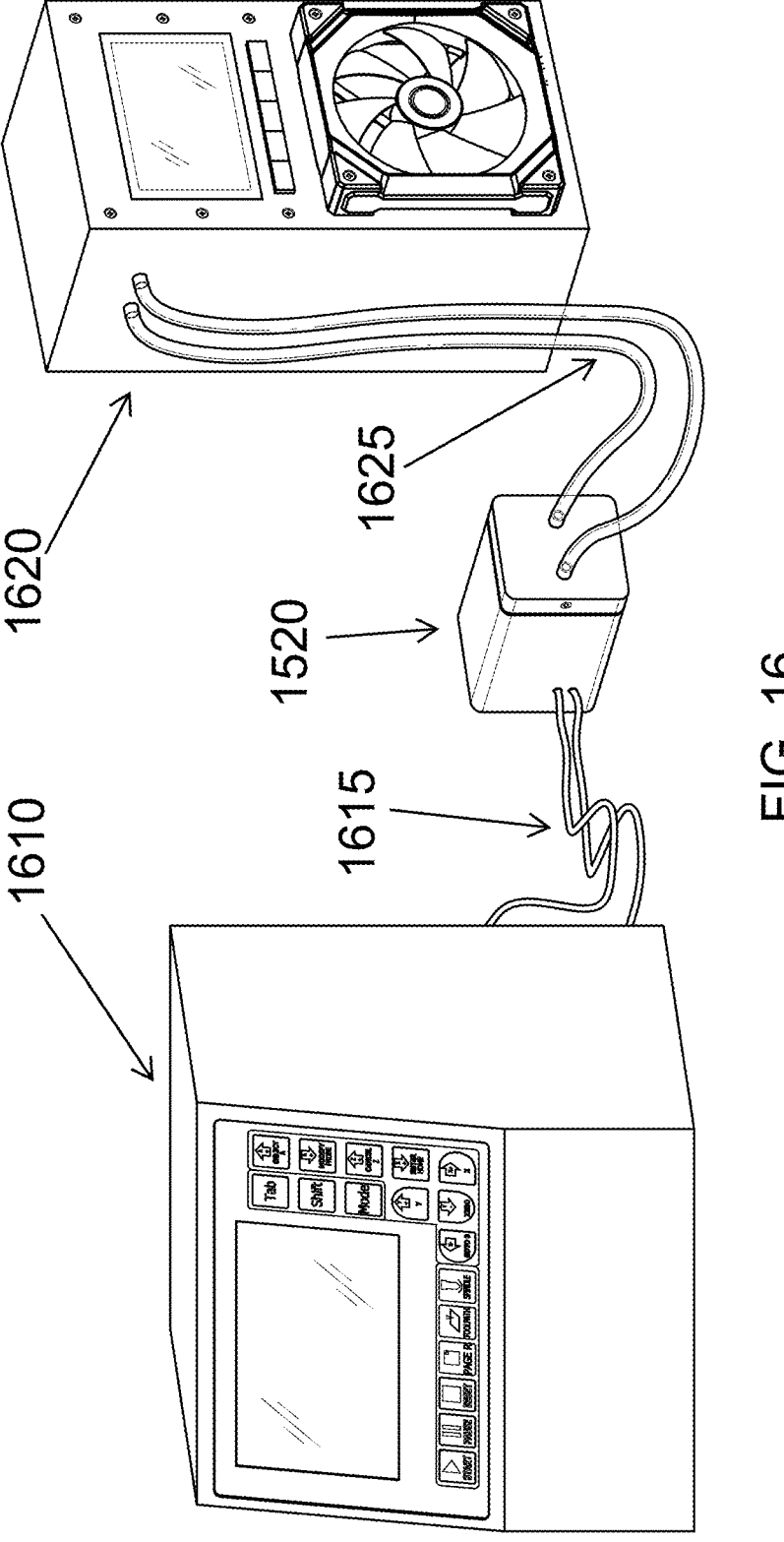

FIG. 16 depicts an external oil cooling system connected to the MPTD applicator in a closed loop heat exchanger configuration (1520) and electronic control unit with driver circuits (1610), power cable to the coils (1615) in this case entering the side of the housing, external cooling unit (1620), oil circulation tubes (1625).

Figure 17A:
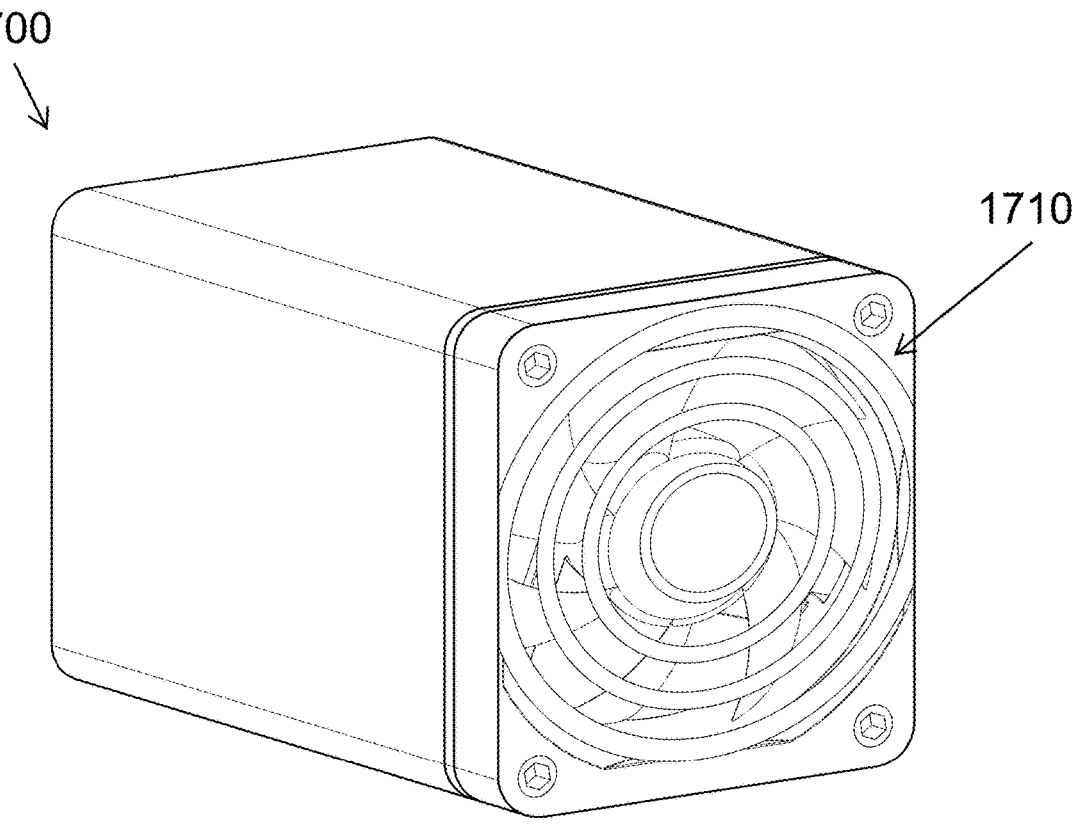

FIG. 17A illustrates a distal view of an MPTD applicator in a forced air-cooling system (1700) configuration comprising a fan (1710) and no heat sink.

Figure 17B:
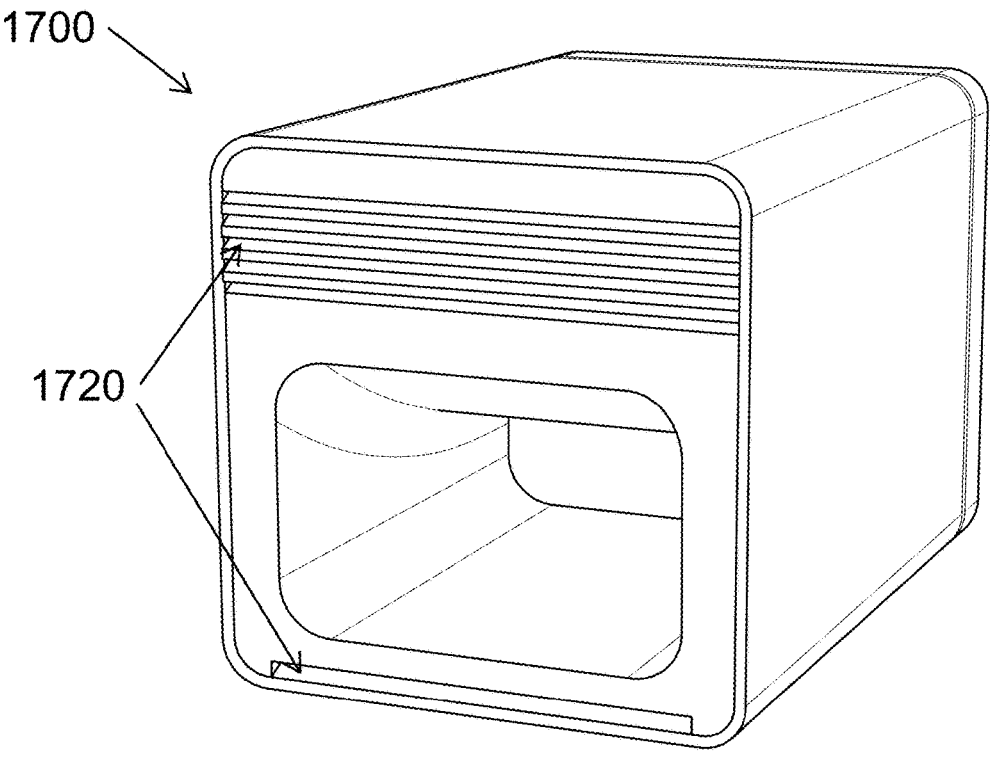

FIG. 17B shows the same forced air-cooling system (1700) as FIG. 17A from a proximal view. The MPTD applicator ventilation slots (1720) to allow flow-through air cooling.

Figure 18:
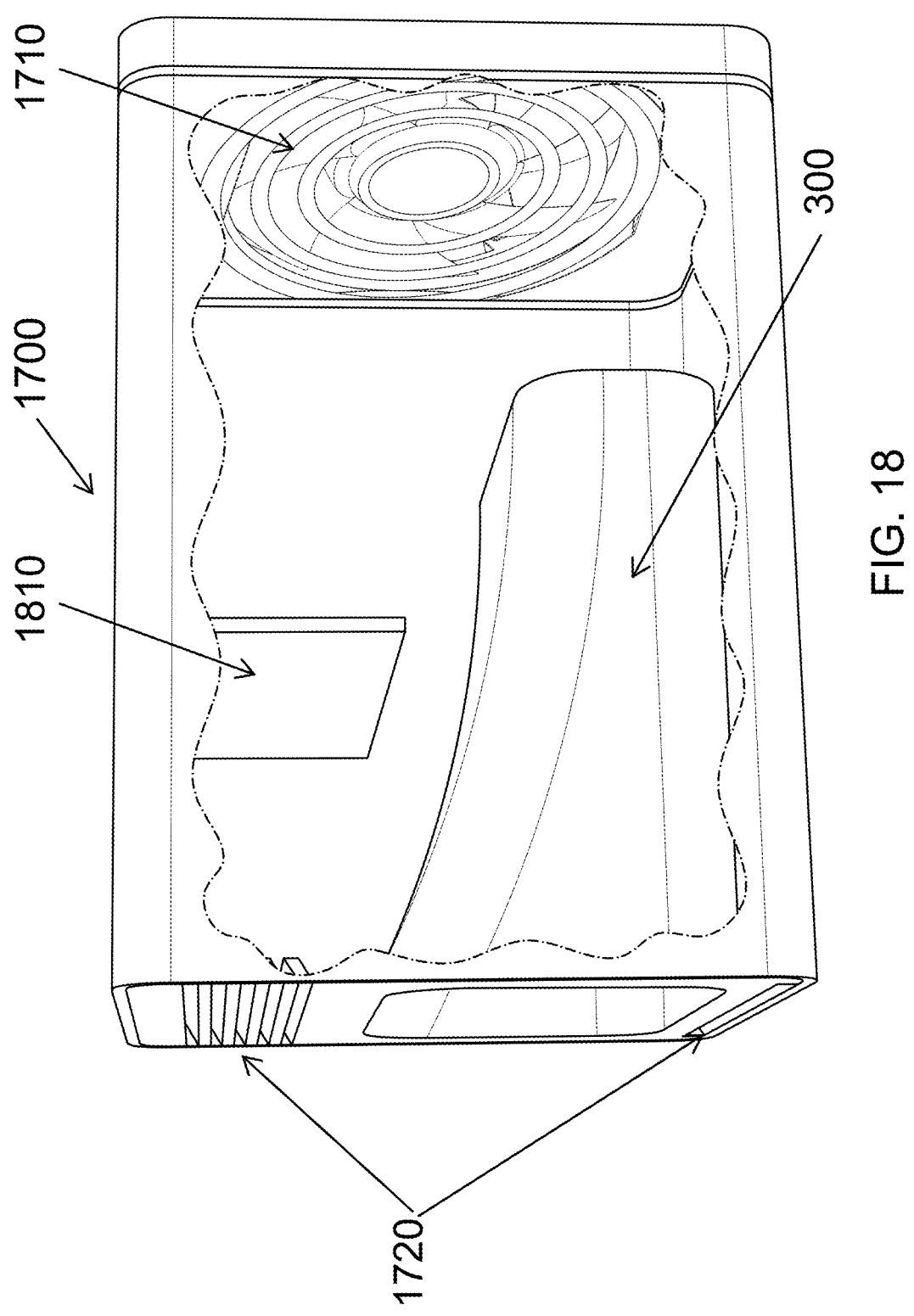

FIG. 18 depicts a cutaway view of the same forced air-cooling system configuration (1700) as FIG. 17A and FIG. 17B with air inlet/outlet slots (1720), fan (1710), treatment chamber (300), and air baffle (1810).

DETAILED DESCRIPTION

The Interstitial Area

The applicator of the present application uses the same fundamental shape and physical design of the original application. There is an outer housing and a treatment chamber encircled by a solenoid. A patient's foot can be inserted through a proximal opening in the housing and into the treatment chamber which then naturally positions the foot into the core of the solenoid. The void, or space between the outer housing and the treatment chamber is illustrated in FIG. 9A and FIG. 9B.

The solenoid windings are in this interstitial area as illustrated in FIG. 9B.

This interstitial area is vitally important to the present application. Normally, placing a source of significant heat within an enclosed area is bad because it results in thermal runaway. But because this space is relatively confined, there is little else in this space except for the coils and connecting cable, and it can be sealed, it becomes useful as a reservoir or duct.

Donning & Doffing

Foot-specific high-power applicators have always struggled with donning and doffing. That is, getting the foot into and out of the device. Traditionally, closures, padding, sizing, straps, and all sorts of manipulations have been mandatory ('067, '302). Or, when the coils have been exposed ('117) the patient must perform contortions to use the device.

The present application shares the same patient user interface as the original application. Donning and doffing through the proximal opening can be performed solely through movement of an extremity associated with the human foot to be inserted into the treatment chamber (FIG. 1, FIG. 9A, FIG. 10A), does not require manual assistance or the use of hands, and does not functionally require wrapping, bending, conforming, deforming, shaping, sizing, padding, stuffing, spreading open, or shoehorning to perform any of inserting the treatment target into the cavity, positioning the treatment target within the cavity, or removing the treatment target from the treatment chamber.

While the ease of donning and doffing is apparent once the design is disclosed, something this straightforward has been elusive in the field of high power MPTDs, and patents '067, '302, '117 and patent application publication US 2002/0151760 A1 make this abundantly clear.

Oil Filled Interstitial

The preferred embodiment of the present application is to fill the Interstitial area with oil. All or a part of the solenoid coils are bathed in this oil, transferring heat from the wires to the oil. The proximal end of the applicator is an anodized aluminum heat sink endcap. The oil is also in contact with this endcap and therefore heat transfers to the heat sink.

Figure 1:
FIG. 1 illustrates an MPTD applicator (100) with a power cable (120) and a patient (110) with a foot inserted into the device (100).
Figure 2:
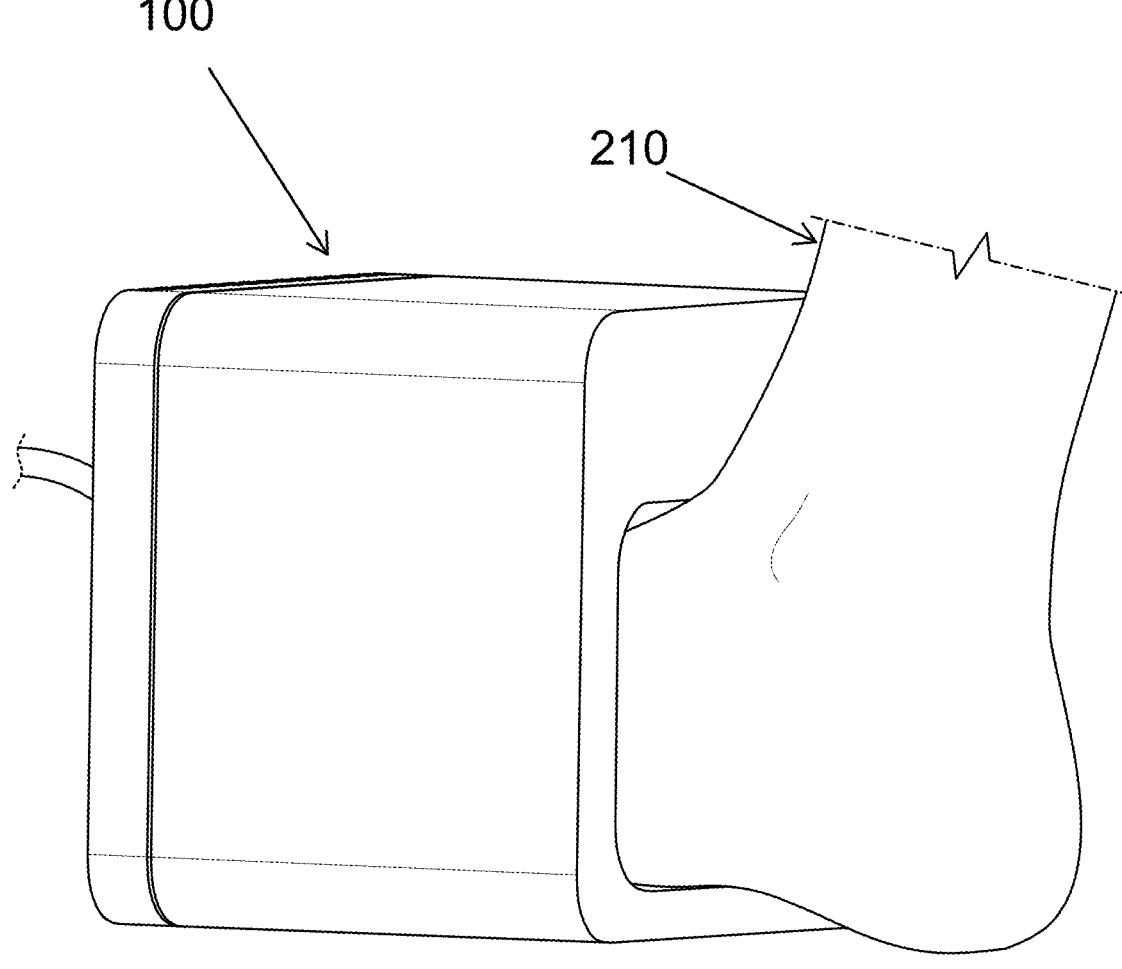
FIG. 2 shows a perspective view of an MPTD applicator (100) with a foot (210) positioned for treatment.
Figure 3:
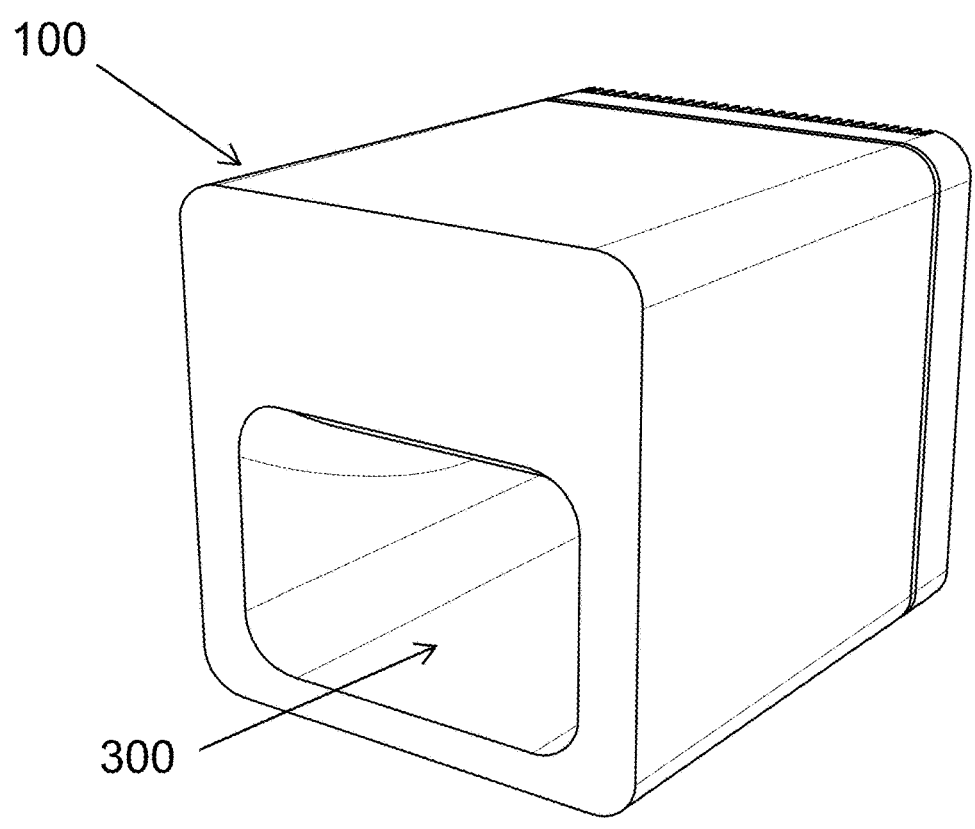
FIG. 3 depicts a perspective view of the MPTD applicator (100) from the proximal end, showing the treatment chamber (300).
Figure 4:
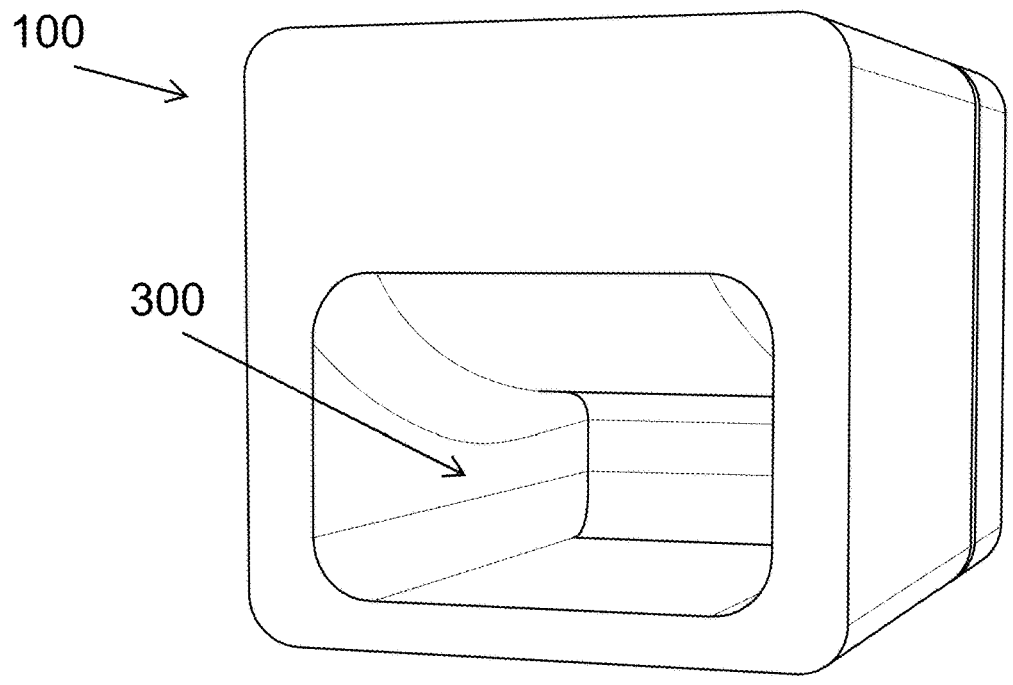
FIG. 4 shows a different perspective view of the MPTD applicator (100) from the distal end, showing more of the treatment chamber (300).

Several adaptations to the original applicator and housing are disclosed, since a liquid-tight interstitial space is preferable:

1) To avoid the need for a gasket at the distal opening of the treatment cavity it is preferred that the end of the treatment zone be closed, as shown in FIG. 1 and FIG. 9A. It was mentioned in the original application at that the opening at the distal end was optional.

2) It is necessary that the treatment zone be formed from a non-conducting material such as plastic (ABS, Polycarbonate, PETG, HDPE.) The necessity of this is to prevent eddy currents which would result in heating and also to allow the magnetic flux to pass through the treatment chamber walls and into the foot being treated. This material must also not react with or break down the oil that will be placed into the interstitial area.

Figure 6:
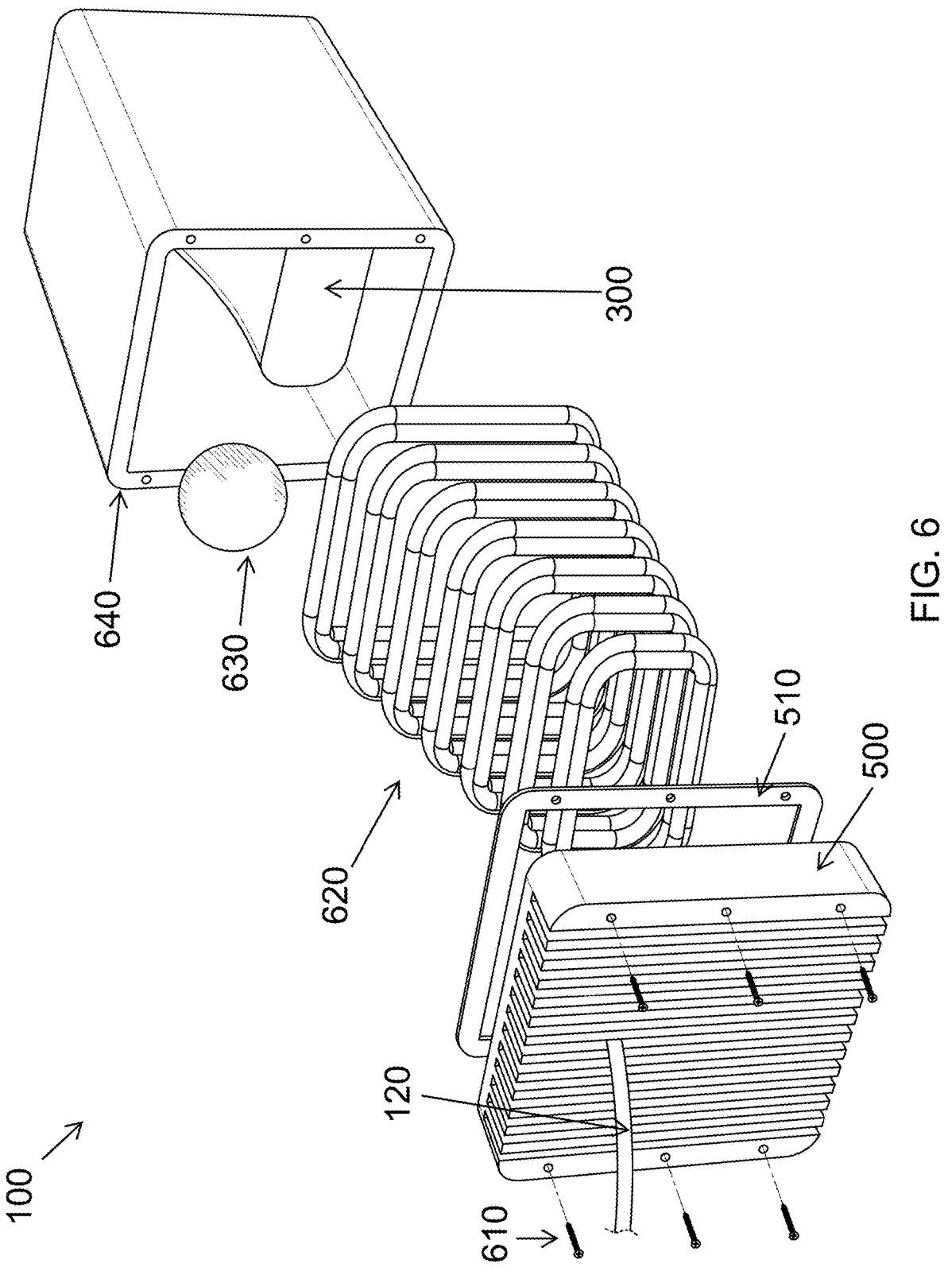
FIG. 6 shows an exploded view of the MPTD applicator (100) with housing (640), solenoid coil (620), thermal expansion ball (630), integrated treatment chamber (300), mounting screws (610), gasket (510), heat sink endcap with fins (500), and power cable (120).
Figure 8:
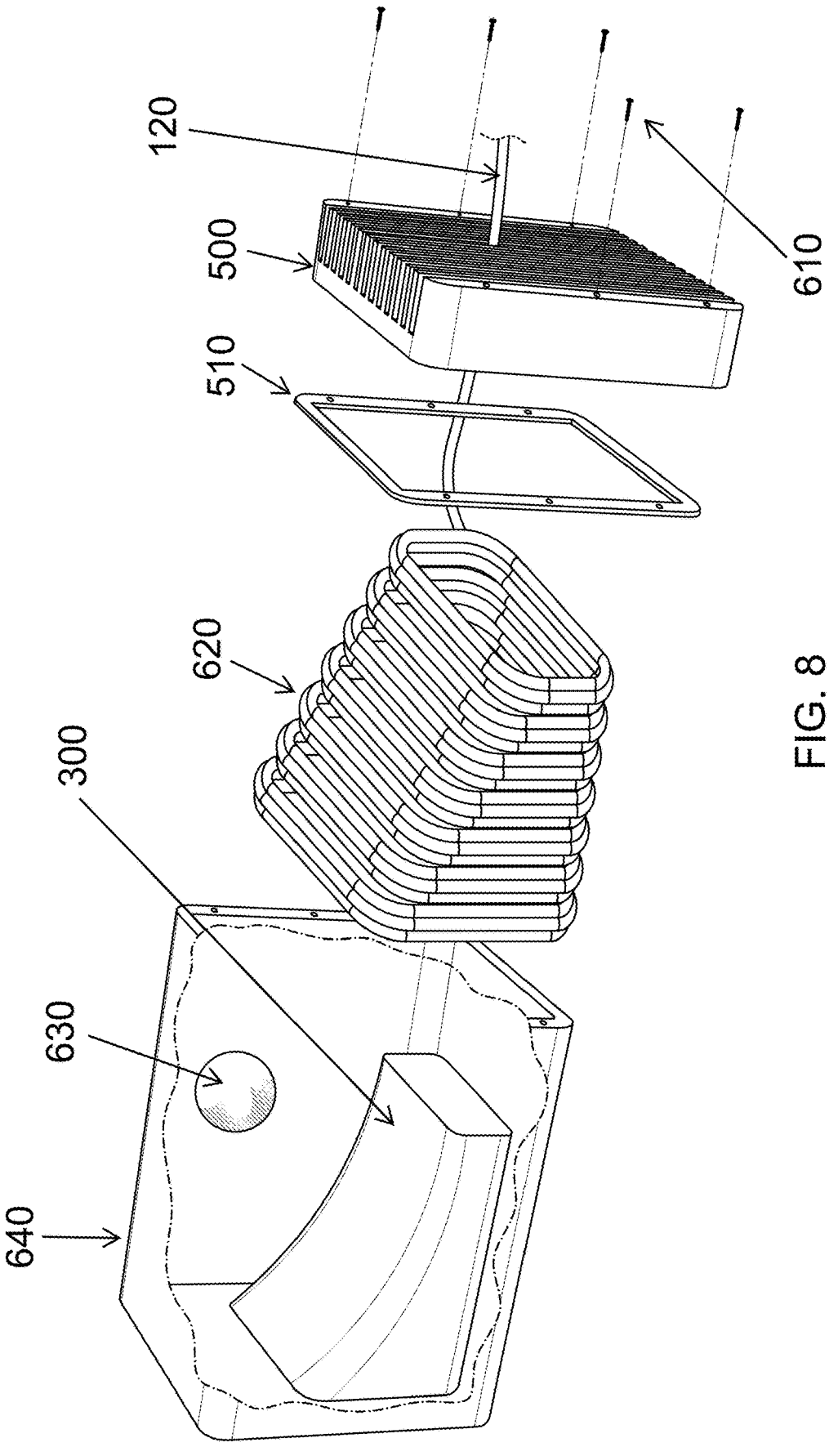
FIG. 8 illustrates an exploded view of the MPTD applicator showing the solenoid coil (620), gasket (510), mounting screws (610), heat sink/radiator with fins (500), power cable (120), and with a cut-away of the housing (640) showing the integrated treatment chamber (300) and thermal expansion ball (630) within.

3) The housing must be made liquid-tight, to prevent the oil from leaking. The fewer seams and seals, the better. FIG. 6 illustrates how the applicator can be configured to have only one flat seal, located at the proximal end. FIG. 8 illustrates that the housing and treatment cavity is formed from one single piece of plastic. FIG. 9A illustrates how the treatment chamber and outer housing are formed into a single piece that can be molded in one shot.

Figure 5:
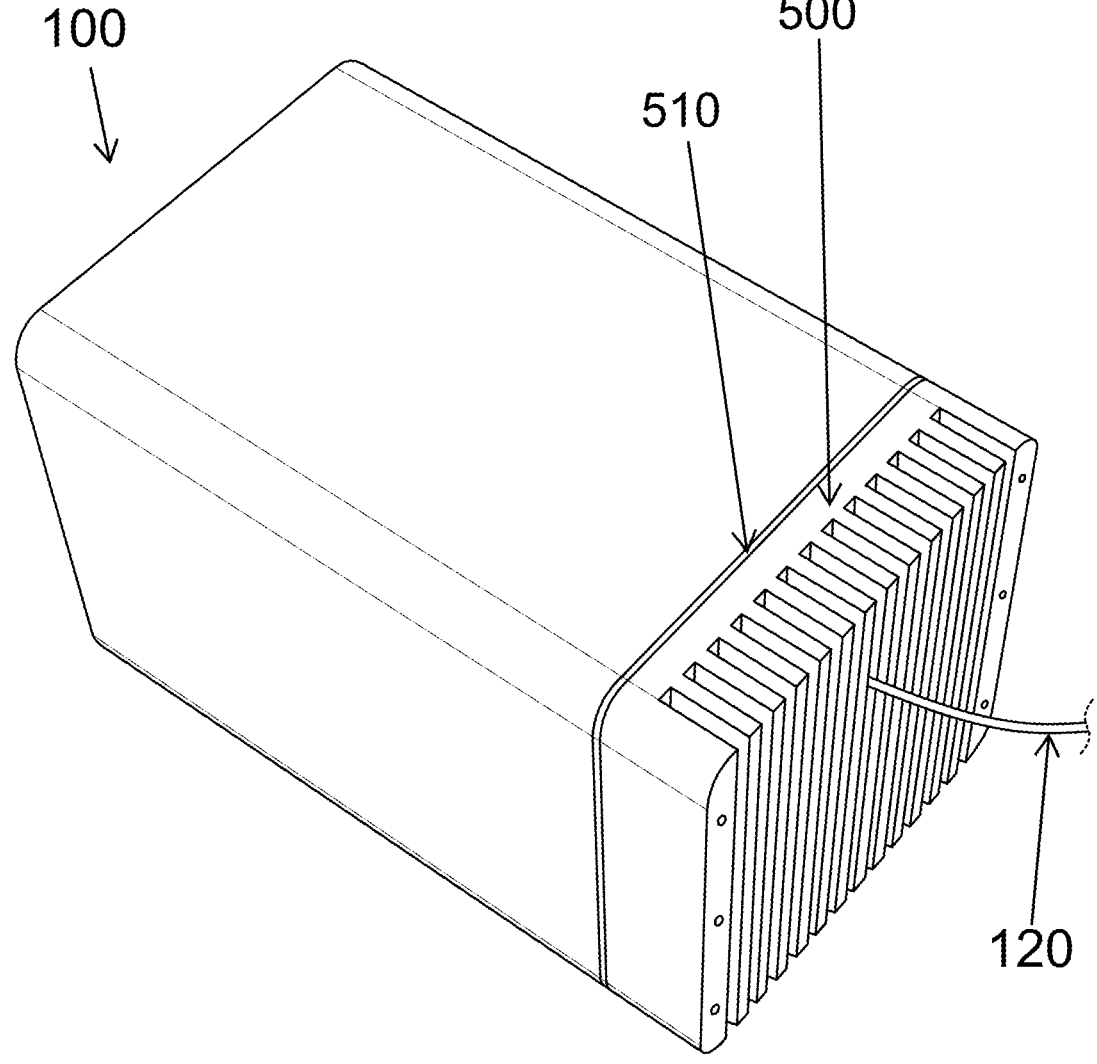
FIG. 5 illustrates a perspective view of the MPTD applicator (100) with heat sink (500), gasket (510), and cable (120) at the distal end.

4) The distal end becomes a heat radiator (FIG. 1, FIG. 5). The radiator is preferably formed from anodized aluminum so as to reduce eddy currents. On the inside the radiator is shown as having a smooth surface (FIG. 11A, FIG. 11B) but if better thermal performance is required then heat-sink grooves can be cut into this surface.

Figure 7:
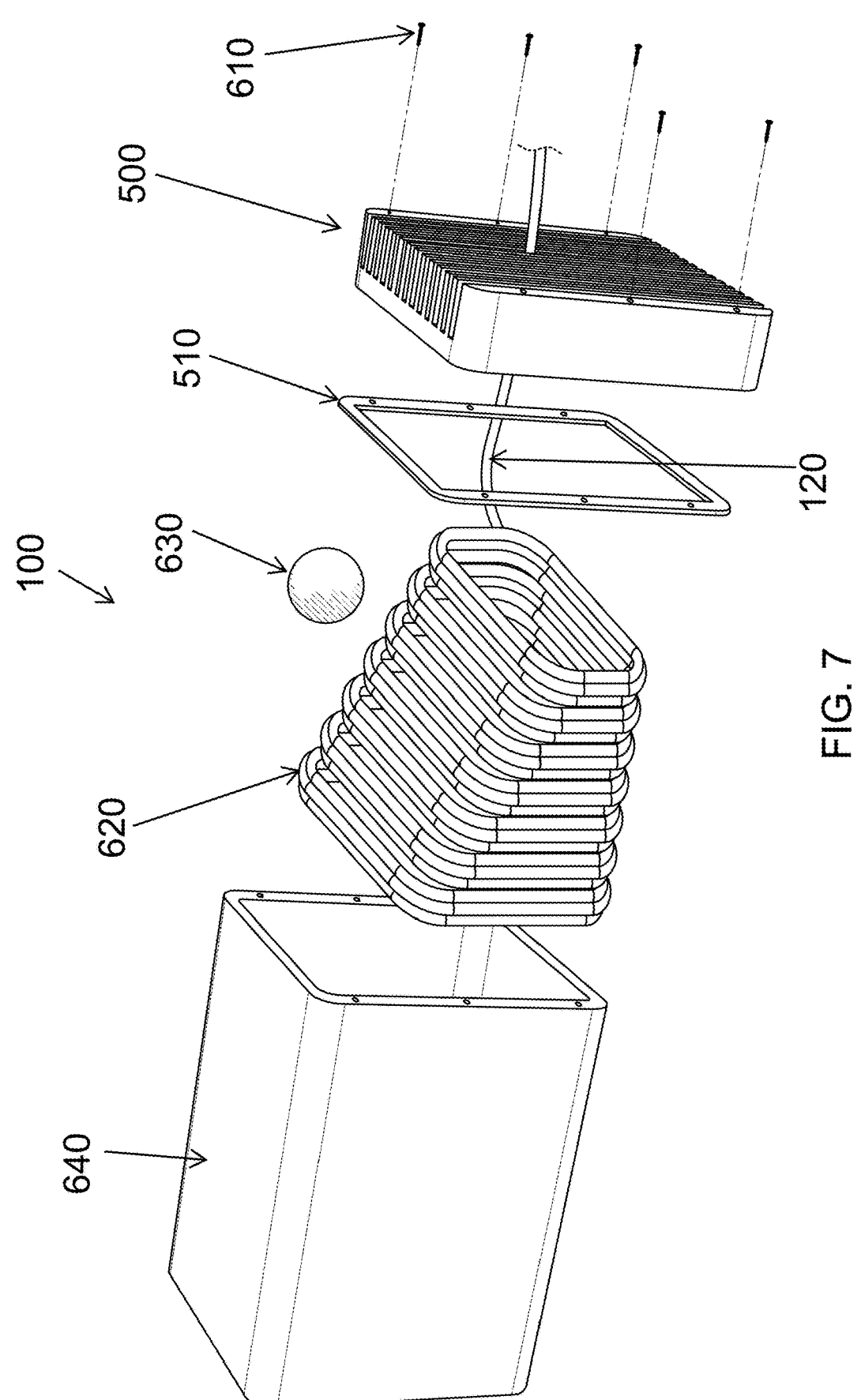
FIG. 7 depicts another exploded view of the MPTD applicator (100) with housing (640), solenoid coil (620), silicon thermal expansion ball (630), mounting screws (610), gasket (510), heat sink endcap with fins (500), and power cable (120).

5) A gasket (FIG. 6, FIG. 7) forms a liquid-tight seal between the housing and the distal endcap radiator. Screws (FIG. 6-8, 11A-11B) tighten the end cap to the housing, compressing the gasket. This forms a liquid-tight seal.

6) The solenoid (FIG. 6-8, 9B-11B) is whatever configuration is desired, and there are no limitations. For a high-powered applicator, it might be constructed from #8 AWG to #2 AWG diameter wire. The solenoid could be a single coil (as illustrated), or it might be a segmented solenoid with multiple coils (not shown). The applicator of the present application is adaptable to any power level and coil configuration. The coil is preferably pre-formed into the correct shape and then is slid onto the treatment chamber where it would be retained in place such as through the use of cable ties or a retaining clip. It is noteworthy that if the windings can be uninsulated (stripped) they will transfer heat to the oil more effectively. The use of a winding spacer will allow bare uninsulated wire to be used and is preferred.

7) The cable from the solenoid (FIG. 5-10A, 11A-11B) must exit the housing. It is illustrates as passing through the distal endcap, but it can be at any location such as the side of the plastic housing. A standard cable gland provides a liquid-tight seal.

8) The thermal expansion of the oil must be accommodated as it is undesirable for the MPTD to perform a "rapid unscheduled disassembly." This is easily done by leaving an air gap of 5% to 10% of the interior volume area. Alternatively, a silicon ball (FIG. 6-10A, 11A-11B) with a diameter of 50 mm can be tossed into the interstitial space. The actual size of the ball or air gap required should be verified based on the intended power, ambient temperature, radiator efficacy, and oil characteristics. Use of the silicon ball will minimize internal sloshing.

9) Finally, the interstitial is filled with a dielectric and thermally conducting oil such a Synthetic Ester (Midel 7131 or Cargill Envirotemp FR3), a Silicone Oil (Dow Corning 561 or Momentive FR3-S), mineral oil or other liquids that are dielectric and thermally conducting. Preference should be given to good thermal conductivity, non-toxicity, and fire retardancy.

In very high-powered systems, it may be beneficial to provide a means of circulation or turbulation of the oil to facilitate heat transfer. In the simplest form this can be accomplished using a hinged flap that has a ferrous or magnetic end such that it vibrates with magnetic pulses from the solenoid. It can also be a small impeller or pump.

Radiator Considerations

The distal-end radiator can indeed be as simple as a standard aluminum heat sink that is flat on the interior surface and has fins on the exterior. For the lower end of high power MPTDs that will be adequate.

But this radiator is rife with both opportunities and pitfalls. To avoid the need for undue experimentation some of those will be discussed here.

An optimal metal to use for the radiator endcap is aluminum because it is cheap, easily machined or formed, and it is an excellent thermal conductor. If aluminum is used, it is preferred that it be anodized. This will reduce conductivity and thereby reduce eddy current induced heating.

The radiator endcap should be spaced as far as possible from the solenoid to minimize parasitic effects such as eddy currents and associated heating. A distance of 50 mm is a reasonable distance. For lower end systems this can be reduced to 25 mm. But when designing the housing and radiator it must be kept in mind that axial flux will be attracted to the radiator endcap.

As the power increases, problems stemming from axial flux and the radiator interacting significantly increase. The easiest remedy is to increase the distance between the radiator and the solenoid coils. In this case, flux reduces at the rate of $1/r^3$ and so even small extra distances have a profound benefit.

Rather than the interstitial-facing surface of the radiator being a flat plate (which begs for eddy current problems, slotting, wherein the slots have a width of 7.5 mm or less and orienting these slots radially or diagonally with respect to the solenoid's flux lines will substantially reduce eddy currents and heating within the radiator endcap. An excellent simple approach would be to crosscut the interior radiator fins so that it more resembles prongs.

Introducing dielectric breaks in the radiator to disrupt conductive pathways will also reduce eddy currents and heating. While most complicated and costly, a simple approach is to make the endcap of plastic and to mold slots that aluminum fins slide through from interior to exterior. The fins can be crosscut on the inside to further reduce eddy current.

Once the heat product of the solenoid coil exceeds the dissipation capacity of the radiator the applicator risks a thermal runaway condition. For this reason, the radiator should be equipped with a temperature sensor that can monitor for absolute limits and also predict the rate of temperature increase. While each applicator will have different characteristics, a rapid rate of temperature rise (dT/dt) would allow the MPTD to be shut down in advance of thermal runaway. (Heat from the coils will take time to transfer to the radiator, and if only the absolute radiator temperature is monitored, the thermal mass within the coils may exceed safety thresholds—the threshold being between 40° C. to 50° C.—even before the radiator temperature reaches a setpoint limit. Therefore, the rate of change of radiator temperature is a leading indicator of internal problems. Of course, adding a temperature sensor close to the coils is another answer.

Active Radiator Cooling (A Fan)

At some point, a passive radiator will be unable to dissipate enough heat to maintain appropriate operating temperatures within the applicator.

The higher that ΔT is between the radiator temperature and the internal oil and also the external ambient air temperature the more efficiently thermal transfer will be.

A good solution is to add a fan to the exterior of the radiator. (Not shown.) How to do this is well understood, and it is a common practice in electronics, especially in power supplies and CPU chips. A typical 120 mm computer fan may be able to remove about 500 watts of heat from the radiator, and a 150 mm computer fan can under ideal conditions remove up to 1000 watts of heat from the radiator.

External Cooling (Closed & Open Loop)

At the highest power levels where the MPTD will be used continually at high power settings, such as in a busy clinic, it is necessary to use an external cooling system. Various types of external cooling systems are commercially available, but the principle is simple: They circulate heat transfer oil to and from a device and either use a radiator with fans, Peltier transfer plates with fans, or a heat pump.

Devices using external oil cooling operate on either a closed loop or an open loop basis.

A closed loop system provides no exchange of fluid between the interstitial and the external heat exchanger. The heat from the solenoid winding transfers to the oil and then must transfer to the radiator which acts like a heat exchanger. This heat is transferred to the external cooling system through a core drilling in a block of the radiator. Liquid from the external cooling system flows through the radiator's block, taking away accumulated heat. Heat from the solenoid windings will transfer heat to the oil bath, and then to the radiator at the distal end. The oil within the interstitial is never circulated through the external cooling system, which allows the use of different types of oil in each loop. Even water can be used in the external cooling loop. (And, indeed, tap water can be used as the simplest of all external cooling systems.)

An open loop system operates fundamentally differently. Oil from the external cooling system flows directly into the interstitial space under modest pressure. Excess oil is recovered, usually from the top of the interstitial space, and is returned to the external cooling device. In this case, the liquid will have direct contact with energized windings which operate at high voltage. It is therefore essential that the oil be correctly selected for dielectric safety. An open loop system is more complicated, but has the highest heat transfer ability for two reasons: 1) Oil flows into and circulates around the coil windings constantly, and 2) There is no inefficient heat exchange through the radiator.

Forced Air Convection Cooling

Non-forced air cooling is unlikely to be viable except at the very lowest range of a high power MPTD. Many high power MPTDs that are suitable for use in clinics (but still at the lower power end) may be able to use simpler forced air convection cooling instead of oil cooling.

For a typical MPTD that produces a few hundred milli-Tesla a high-performance computer fan that is 120 mm or 150 mm may have enough thermal transfer ability. A 120 mm high performance fan can move 40~50 CFM and a 150 mm high performance fan can move 60-100 CFM.

In a forced air configuration, the cooling fan would be mounted in place of the radiator. Room temperature air would be drawn into the interstitial area. This air would naturally flow through the interstitial area, across the coil windings, and out through vent holes. A plastic baffle can be used to direct airflow directly to the coils.

In a forced air configuration, it is particularly valuable that the windings be uninsulated and be held into place with a winding spacer. This will maximize thermal transfer with the passing air.

A temperature probe should be used to ensure a safe coil temperature, and this can also be used to PWM the fan speed so that the fan operates at an optimal speed for each portion of the treatment protocol.

Of course, alternative configurations are possible, such as using an external vacuum or blower that attaches to a port on the back or side of the applicator. Such an external air handler would provide higher performance.

SUMMARY

The magnetic pulse therapy applicator for treating a human foot comprises a treatment chamber configured to receive at least a portion of a human foot, one or more coils disposed around the treatment chamber and configured to generate magnetic pulses therein when energized, an outer housing enclosing the treatment chamber and the coils, and an interstitial space between the outer housing and the treatment chamber containing a heat transfer medium configured to transfer heat away from the coils. The outer housing defines an opening for insertion and removal of the foot. In some embodiments, the heat transfer medium is air, and a forced air mechanism circulates air through the interstitial space to remove heat.

Alternatively, a radiator in thermal contact with the heat transfer medium dissipates heat externally, with a fan positioned within the interstitial space, external to the housing, on the opposite side of the radiator from the interstitial space, or in any combination thereof, directing air across the radiator. The radiator may include features to reduce eddy currents or parasitic effects, such as a minimum distance of 25 mm from the nearest coil, anodized aluminum construction, slots of 7.5 mm or less in width oriented radially or diagonally relative to magnetic flux lines, or dielectric breaks disrupting conductive pathways.

In other embodiments, the heat transfer medium is a thermally conductive dielectric oil, such as ester oil, silicone oil, or mineral oil, immersing at least a portion of the coils, with optional circulation through an open-loop or closed-loop system to a cooling unit, and a radiator in thermal contact with the oil for external heat dissipation. A thermal expansion accommodation structure, comprising an air gap or compressible object, accommodates volumetric or pressure changes due to temperature variations. A temperature sensor and electronic control unit monitor temperature and its rate of change, adjusting operation to prevent overheating and enable sustained operation at magnetic pulse levels of 200 mT or greater without cooling pauses or device replacement.

The coils, formed from wire of #8 AWG or larger gauge, deliver magnetic pulses to the toes, forefoot, ankle, and heel simultaneously, with a winding spacer between turns permitting uninsulated wire for enhanced heat transfer. The treatment chamber, constructed from ABS, PLA, polycarbonate, PETG, or HDPE, conforms to the foot's contours, tapering distally, with an average height at least 20% less than its average width, and an opening allowing foot insertion and removal without vertical lifting or device manipulation.

In some embodiments, the coils form a solenoid, positioning the foot within its core. The magnetic pulse therapy system incorporates these elements, with the treatment chamber having a distal cross-sectional area at least 20% smaller than a proximal area or an average height 20% less than its width, coils generating pulses of at least 200 mT, and a heat transfer system using thermally conductive dielectric oil with a radiator, open-loop, or closed-loop cooling unit.

The system sustains operation without exceeding safe temperature limits, supported by a winding spacer and thermal expansion structure, and may be energized by pulses with a nominal voltage of at least 235 volts, aggregate amperage of at least 1000 amperes, aggregate instantaneous power of at least 250,000 watts, or a combination exceeding ICNIRP guidelines by at least five times. In a further embodiment, the applicator, sized for a human foot, includes coils generating magnetic pulses and a cooling system with a forced air mechanism, dielectric oil bath, or both.

What is claimed is:

1. A magnetic pulse therapy applicator for treating a human foot, comprising:
   a treatment chamber configured to receive all or a portion of the human foot, the treatment chamber having an average height at least 20% less than an average width at a distal end;
   one or more coils disposed around the treatment chamber and configured to generate magnetic pulses within the treatment chamber when energized;
   an outer housing enclosing the treatment chamber and the one or more coils, the outer housing defining an opening into the treatment chamber for insertion and removal of the human foot; and
   an interstitial space between the outer housing and the treatment chamber containing the one or more coils and a heat transfer medium that surrounds the one or more coils and transfers heat generated by the one or more coils away from the one or more coils.

2. The device of claim 1, wherein the heat transfer medium is air, and the device further comprises a forced air mechanism configured to circulate the air through the interstitial space to remove heat therefrom.

3. The device of claim 1, further comprising a radiator positioned in thermal contact with the heat transfer medium and configured to radiate heat externally from the device.

4. The device of claim 3, further comprising a fan that provides forced air across at least a portion of the radiator either within the interstitial space, on an exterior, opposite side of the radiator from the interstitial space, or both.

5. The device of claim 3, wherein the device further comprises a fan configured to direct forced air across at least a portion of the radiator, the fan positioned:
   (a) within the interstitial space;
   (b) external to the outer housing;
   (c) on an opposite side of the radiator from the interstitial space; or
   (d) in any combination of (a), (b), and (c).

6. The device of claim 3, wherein the radiator is configured to minimize eddy currents, parasitic effects, or both within the radiator, the radiator comprising at least one of the following:
   (a) the radiator positioned at least 25 mm from a nearest one of the one or more coils;
   (b) the radiator formed of anodized aluminum;
   (c) the radiator defining slots having a width of 7.5 mm or less, the slots oriented radially or diagonally relative to magnetic flux lines of the one or more coils and positioned on a side of the radiator adjacent to the interstitial space; or
   (d) the radiator including dielectric breaks configured to disrupt conductive pathways therein.

7. The device of claim 1, wherein the heat transfer medium comprises a thermally conductive dielectric oil, the one or more coils being at least partially immersed therein.

8. The device of claim 7, wherein the thermally conductive dielectric oil comprises one selected from the group consisting of ester oil, silicone oil, and mineral oil.

9. The device of claim 7, further comprising a thermal expansion accommodation structure, the structure comprising at least one of an air gap or a compressible object configured to absorb volumetric or pressure changes due to temperature variations.

10. The device of claim 7, wherein a radiator is positioned in thermal contact with the thermally conductive dielectric oil and configured to radiate heat external to the device.

11. The device of claim 7, wherein the thermally conductive dielectric oil is configured to circulate through a closed loop to a cooling unit.

12. The device of claim 7, wherein the thermally conductive dielectric oil is configured to circulate through an open loop to a cooling unit.

13. The device of claim 1, further comprising a temperature sensor configured to monitor a temperature within the device and an electronic control unit configured to adjust operation of the device to prevent overheating.

14. The device of claim 13, wherein the electronic control unit is configured to monitor a rate of temperature change within the device and to adjust operation of the device to prevent overheating.

15. The device of claim 1, wherein the device is configured to allow sustained operation without exceeding safe temperature limits at power levels capable of producing magnetic pulses of 200 mT or greater throughout an entire treatment session, without requiring a pause for cooling, and without requiring replacement with a cooler device of the same type.

16. The device of claim 1, wherein the one or more coils are constructed from wire having a gauge of #8 AWG or larger diameter.

17. The device of claim 16, wherein the one or more coils are configured to concurrently deliver magnetic pulses to all of the human foot's toes, forefoot, ankle, and heel.

18. The device of claim 16, further comprising a winding spacer positioned between turns of the one or more coils, the winding spacer configured to enable use of uninsulated wire for enhanced heat transfer.

19. The device of claim 1, wherein the treatment chamber is constructed from a polymeric material resistant to degradation by oil, selected from the group consisting of acrylonitrile butadiene styrene (ABS), polycarbonate, polyethylene terephthalate glycol (PETG), high-density polyethylene (HDPE), nylon, polylactic acid (PLA), polypropylene (PP), or combinations thereof.

20. The device of claim 1, wherein the treatment chamber is shaped to conform to contours of a human foot and tapers distally to accommodate toes belonging to the human foot.

21. The device of claim 1, wherein the opening is configured to allow insertion and removal of the human foot solely by movement of the human foot without requiring vertical lifting or device manipulation.

22. The device of claim 1, wherein the one or more coils form a solenoid, and the treatment chamber is configured such that insertion of the human foot into the treatment chamber positions the human foot within a core of the solenoid.

23. A magnetic pulse therapy system for treating a human foot, comprising:

an applicator including:

a treatment chamber configured to receive at least a portion of the human foot, the treatment chamber configured to conform to contours of the human foot, wherein the treatment chamber has at least one of the following properties:

(a) a cross-sectional area of a distal portion of the treatment chamber is at least 20% smaller than a cross-sectional area of a more proximal portion of the treatment chamber; or (b) an average height of a cross section of the treatment chamber is at least 20% less than an average width of that cross section;

one or more coils comprising wire having a gauge of #8 AWG or larger, the one or more coils configured to generate magnetic pulses with a peak flux density of at least 200 mT within the treatment chamber when energized;

an outer housing enclosing the treatment chamber and the one or more coils, the outer housing defining an opening into the treatment chamber for insertion and removal of the human foot;

an interstitial space between the outer housing and the treatment chamber containing the one or more coils and a thermally conductive dielectric oil, the one or more coils being at least partially immersed in the thermally conductive dielectric oil; and a heat transfer system configured to transfer heat away from the one or more coils via the thermally conductive dielectric oil, the heat transfer system comprising at least one of:

(a) a radiator in thermal contact with the thermally conductive dielectric oil and ambient air external to the interstitial space;

(b) an open-loop circulation system connected to a cooling unit; or (c) a closed-loop circulation system connected to a cooling unit.

24. The applicator of claim 23, wherein the one or more coils form a solenoid around the treatment chamber and wherein an inserted foot would be within the core of the solenoid.

25. The applicator of claim 23, wherein the applicator is configured to allow sustained operation without exceeding safe temperature limits at power levels capable of producing magnetic pulses of 200 mT or greater throughout an entire treatment session, without requiring a pause for cooling, and without requiring replacement with a cooler applicator of the same type.

26. The applicator of claim 25, further comprising a winding spacer configured to enable the one or more coils to comprise uninsulated wire for enhanced heat transfer.

27. The applicator of claim 23, further comprising a thermal expansion accommodation structure configured to absorb volumetric or pressure changes due to temperature variations.

28. The applicator of claim 23, wherein the one or more coils are energized by electrical pulses having at least one of: a nominal voltage of at least 235 volts, an aggregate amperage of at least 1000 amperes, an aggregate instantaneous power of at least 250,000 watts, or a voltage and amperage combination sufficient to exceed ICNIRP general public guidelines by at least five times.

* * * * *